(12) United States Patent
Martin

(10) Patent No.: US 8,589,087 B2
(45) Date of Patent: Nov. 19, 2013

(54) SYSTEMS, METHODS, AND APPARATUS FOR MONITORING CORROSION OR CORROSIVE CONTAMINANTS ASSOCIATED WITH LIQUID FUEL

(75) Inventor: Paul Joseph Martin, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 196 days.

(21) Appl. No.: 12/844,947

(22) Filed: Jul. 28, 2010

(65) Prior Publication Data

US 2012/0023894 A1 Feb. 2, 2012

(51) Int. Cl.
*F02G 1/00* (2006.01)
*G01B 3/44* (2006.01)

(52) U.S. Cl.
USPC .......................... 702/34; 60/39.091

(58) Field of Classification Search
USPC ................. 702/34; 60/39.091; 3/34
See application file for complete search history.

(56) References Cited

U.S. PATENT DOCUMENTS

| | | | |
|---|---|---|---|
| 5,517,427 A | 5/1996 | Joyce | |
| 6,121,628 A * | 9/2000 | Rising | 250/573 |
| 6,526,741 B2 | 3/2003 | Whitehead et al. | |
| 6,632,257 B1 | 10/2003 | Feitelberg et al. | |
| 6,644,095 B2 | 11/2003 | Van Mullekom et al. | |
| 6,810,718 B2 | 11/2004 | Wilson et al. | |
| 7,258,098 B2 | 8/2007 | Kim | |
| 7,265,559 B1 * | 9/2007 | Hladky et al. | 324/700 |
| 7,457,785 B1 | 11/2008 | Greitzer et al. | |
| 2002/0153873 A1 * | 10/2002 | Shapiro et al. | 324/71.2 |
| 2005/0274611 A1 * | 12/2005 | Schlichting | 204/401 |
| 2006/0006137 A1 * | 1/2006 | Niblock | 216/41 |
| 2007/0072137 A1 * | 3/2007 | Peluso et al. | 431/13 |
| 2007/0079593 A1 * | 4/2007 | Fujii et al. | 60/39.27 |
| 2008/0141780 A1 * | 6/2008 | Wavering et al. | 73/723 |
| 2008/0216395 A1 | 9/2008 | Schaeffer et al. | |
| 2011/0095190 A1 * | 4/2011 | Kommareddy et al. | 250/364 |
| 2011/0138813 A1 * | 6/2011 | Sandvik et al. | 60/740 |
| 2011/0251721 A1 * | 10/2011 | Hefner et al. | 700/275 |

* cited by examiner

*Primary Examiner* — Marc Armand
*Assistant Examiner* — Michael Dalbo
(74) *Attorney, Agent, or Firm* — Sutherland Asbill & Brennan LLP

(57) ABSTRACT

Certain embodiments of the invention may include systems, methods, and apparatus for monitoring corrosion or corrosive contaminants associated with liquid fuel. According to an example embodiment of the invention, a method is provided for monitoring and predicting corrosion. The method can include monitoring corrosion or corrosive contaminants associated with liquid fuel in a fuel supply system of a gas turbine, predicting, based at least in part on the monitoring, a cumulative level of corrosion of one or more components associated with a gas turbine, and outputting information associated with the monitoring.

20 Claims, 2 Drawing Sheets

SYSTEMS, METHODS, AND APPARATUS FOR MONITORING CORROSION OR CORROSIVE CONTAMINANTS ASSOCIATED WITH LIQUID FUEL

FIELD OF THE INVENTION

This invention generally relates to detection of contaminants in fuel, and, in particular, to monitoring corrosivity of liquid fuel for use in gas turbines.

BACKGROUND OF THE INVENTION

Certain fuel contaminants can accelerate corrosion in components associated with a gas turbine. Liquid fuels used for combustion in gas turbines typically include distillates and ash-bearing hydrocarbon-based fuels. Contaminants may be present in the fuel and may cause degradation of tanks, pipes, valves, alloy coatings, and other components associated with the delivery of fuel and the operation of the gas turbine. Salt water, sulfur, sodium, vanadium, potassium, calcium, lead, etc. may act alone or in combination to cause corrosion. For example, oxides of sulfur and vanadium may react with other contaminants to form sulfates and vanadates that are corrosive at high temperatures.

Typically, the presence of contaminants in fuel can damage protective oxide layers on the surface of gas turbine components such as combustors, transition pieces, turbine buckets, and other components in the hot gas path (HGP). Furthermore, contaminants in the compressor inlet air, injected steam, and water may contribute significantly to corrosion. Excessive corrosion can lead to component failure, resulting in major turbine component replacement, costly repairs and significant machine down time. Low-level quantities of certain corrosive elements (1 part per million or greater) in the fuel are sufficient to cause hot corrosion.

Detecting and quantifying the full complement of liquid fuel contaminants in their elemental form in a continuous on-line, real-time basis is technologically challenging, and has been explored through conversion of laboratory-grade methods to field-deployable equipment including X-Ray Fluorescence (XRF), Pulsed Neutron Activation Analysis (PNAA), Rotating Disk Electrode Atomic Emission Spectroscopy (RDE-AES), Electron Paramagnetic Resonance (EPR) and Inductively Coupled Plasma (ICP). The leading technology for this type of measurement is XRF for which several vendors have supplied on-line real-time systems capable of measuring hydrocarbon-based liquid fuels, with the primary focus on measuring sulfur in refinery fuel for the purpose of achieving ultra-low sulfur diesel. These on-line XRF systems may be able to detect the heavier metal contaminants (vanadium and lead) to the single-digit parts per million levels; however, these XRF systems do not appear capable of detecting the lighter metals (sodium, potassium, or calcium) at low levels.

BRIEF SUMMARY OF THE INVENTION

Some or all of the above needs may be addressed by certain embodiments of the invention. Certain embodiments of the invention may include systems, methods, and apparatus for monitoring corrosion or corrosive contaminants associated with liquid fuel.

According to an example embodiment of the invention, a method is provided for monitoring and predicting corrosion. The method can include monitoring corrosion or corrosive contaminants associated with liquid fuel in a fuel supply system of a gas turbine; predicting, based at least in part on the monitoring, a cumulative level of corrosion of one or more components associated with a gas turbine; and outputting information associated with the monitoring.

According to another example embodiment, a system is provided for monitoring and predicting corrosion. The system may include a gas turbine, at least one fuel supply line for delivering liquid fuel to the gas turbine, one or more sensors in communication with the at least one fuel supply line, at least one memory for storing data and computer-executable instructions, and at least one processor configured to access the at least one memory. The at least one processor is further configured to execute the computer-executable instructions for monitoring, with the one or more sensors, corrosion or corrosive contaminants associated with the liquid fuel. The at least one processor is further configured to execute the computer-executable instructions for predicting, based at least in part on the monitoring, a cumulative level of corrosion of one or more components associated with a gas turbine, wherein the one or more components comprise at least one of a liquid fuel tank, liquid fuel piping, or hot gas path components associated with the gas turbine. The at least one processor is further configured for outputting a signal associated with the monitoring.

According to another example embodiment, an apparatus is provided for monitoring and predicting corrosion. The apparatus includes at least one memory for storing data and computer-executable instructions, and at least one processor configured to access the at least one memory, and further configured to execute the computer-executable instructions for monitoring, with one or more sensors, corrosion or corrosive contaminants associated with liquid fuel in a fuel supply system of a gas turbine; predicting, based at least in part on the monitoring, a cumulative level of corrosion of one or more components associated with a gas turbine wherein the one or more components comprise at least one of a liquid fuel tank, liquid fuel piping, or hot gas path components associated with the gas turbine. The at least one processor is further configured for outputting a signal associated with the monitoring.

Other embodiments and aspects of the invention are described in detail herein and are considered a part of the claimed invention. Other embodiments and aspects can be understood with reference to the following detailed description, accompanying drawings, and claims.

BRIEF DESCRIPTION OF THE FIGURES

Reference will now be made to the accompanying tables and drawings, which are not necessarily drawn to scale, and wherein.

DETAILED DESCRIPTION OF THE INVENTION

Figure 1:
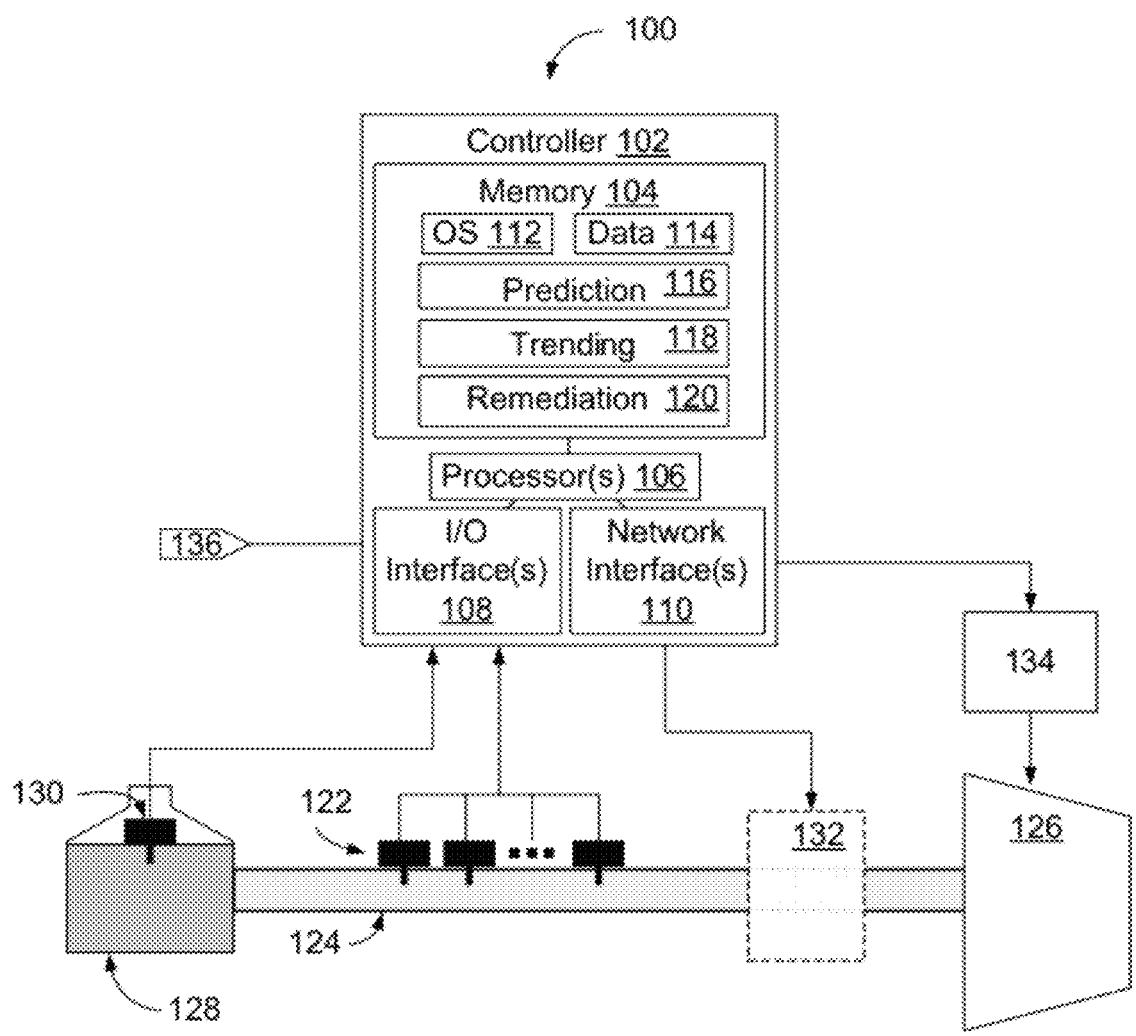
FIG. 1 is a block diagram of an illustrative corrosive sensing system according to an example embodiment of the invention.

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. Certain embodiments of the invention may enable measuring corrosivity in gas turbine liquid fuels.

Certain example embodiments of the invention may include on-line, real-time corrosivity measurements of gas turbine liquid fuels, for example, to determine, record, and trend the associated hot corrosion that may occur on the hot gas path (HGP) components following fuel combustion. According to an example embodiment of the invention, linear polarization resistance (LPR) corrosion sensors may be utilized to monitor liquid fuel in pipes that supply the fuel to the gas turbine combustors. Certain embodiments of the invention may utilize LPR sensor corrosion rates and electrode material properties to assess the gas turbine fuel corrosivity. The information from the LPR sensors may be used in conjunction with information obtained from water sensors, density sensors, and/or viscosity sensors to characterize and assess changes relating to the presence of corrosive contaminants in the fuel. This corrosivity information may be utilized to assess the cumulative HGP corrosion damage occurring from fuel combustion.

In certain example embodiments, the LPR sensors may utilize multiple electrodes in direct contact with the fluid. The LPR electrodes may include sacrificial electrode material that may match the piping or gas turbine material so that corrosion degradation over time, as caused by the corrosivity of the fuel, may be related to the excitation and degradation of the electrode material. In certain example embodiments, the LPR sensors may measure a general corrosion rate, a localized pitting-factor rate, and/or other parameters relating to the corrosion measurement. For example, measurements of the harmonic distortion and a Stern-Geary constant may be utilized to determine the integrity of the sensor signals.

According to example embodiments of the invention, LPR sensors in the gas turbine liquid fuel may be utilized for measuring specific corrosive compounds (e.g., salt water, which consists primarily of sodium) that if combusted could cause hot corrosion in the HGP. According to example embodiments, monitoring and trending of the corrosivity through the various LPR sensor corrosion rates may be utilized to develop transfer functions that relate fuel corrosivity to accumulated hot corrosion in the HGP of the gas turbine. Multiple LPR sensors using various electrode materials may be utilized to characterize and detect the corrosive elements of interest.

Certain example embodiments of the invention may include one or more of (1) identifying the proper LPR sensor electrode material to interact with the liquid fuel contaminants that cause hot corrosion; (2) placing the LPR sensor at the proper location and orientation within the liquid fuel stream to ensure that the electrode material interacts with the contaminants; (3) assessing the corrosivity of the liquid fuel based on LPR sensor measurements; (4) predicting the downstream effect of the fuel corrosivity on HGP hot corrosion; (5) recording and trending the predicted hot corrosion to determine the cumulative effect on the HGP; and (6) establishing maintenance factors and HGP component lifetime assessments based on measurements. In certain example embodiments of the invention, corrosion inhibitor may be injected into the fuel supply lines in response to the LPR measurements.

According to example embodiments of the invention, various sensors, fuel supply lines, controllers, and processors, may be utilized for monitoring, predicting, and assessing corrosion, and will now be described with reference to the accompanying figures.

FIG. 1 is a block diagram of an illustrative corrosive sensing system 100 according to an example embodiment of the invention. The system 100 may include a controller 102 that may include a memory 104, one or more processors 106, one or more input/output interfaces 108, and/or one or more network interfaces 110. According to example embodiments, the memory 104 may include an operating system 112 and data 114. The memory 104 may also include computer-executable modules for processing input and data. For example, the memory 104 may include a prediction module 116, a trending module 118, and a remediation module 120.

In certain example embodiments, the system 100 may include one or more sensors 122 in communication with fuel that is being supplied (via one or more fuel supply lines 124) to a gas turbine 126. Certain embodiments of the invention may include an in-tank sensor 130 in communication with fuel that is being stored in a fuel tank 128, for example. According to certain example embodiments, the system 100 may include one or more corrosion inhibition injectors 132 for releasing corrosion inhibitor into the fuel lines 124. In certain example embodiments, the corrosion inhibitor may be controllably released into the fuel lines 124 in response, at least in part, to the measurements by the sensors 122, 130, or by control signals provided by the remediation module 120.

According to certain example embodiments of the invention, the controller 102 may receive sensor measurement information from the sensors 122, 130, and may provide prediction or trending information that may be utilized for making or modifying maintenance schedules 134 for the turbine 126, fuel supply lines, 124, tank 128, and/or other components associated with the gas turbine. Certain embodiments of the invention may include auxiliary inputs and/or outputs 136 for communication with operators or additional equipment.

In certain example embodiments of the invention, the sensors 122, 130 may be utilized for monitoring corrosion or corrosive contaminants associated with liquid fuel in a fuel supply system of a gas turbine. According to an example embodiment, the prediction module 116 may be operable for predicting a cumulative level of corrosion in the or of the one or more components associated with a gas turbine based at least in part on the monitoring. According to example embodiments of the invention, information associated with the monitoring, prediction, and/or trending may be output and utilized by operators, or may be utilized in maintenance schedules 134 or for controlling corrosion inhibitor injectors 132. Certain example embodiments may include predicting the cumulative level of corrosion and estimating a remaining lifetime associated with the one or more components associated with the gas turbine 126. In certain example embodiments, at least a portion of the information associated with the monitoring may be stored, and a corrosive event trend may be determined based at least in part on the stored information. In example embodiments, a cumulative level of corrosion in the or of the one or more components associated with a gas turbine may be predicted based at least in part on the monitoring.

Certain example embodiments of the invention provide systems, methods and apparatus for conducting online, continuous, and/or in-situ measurements. In certain example embodiments, corrosion or corrosive contaminants associated with liquid fuel may be monitored or measured using one or more linear polarization resistance (LPR) sensors. According to certain example embodiments, the one or more sensors may include sacrificial electrodes. In an example embodiment of the invention, measurement information associated with the monitoring may be stored in the memory 104, and at least a portion of the information may be utilized for determining a corrosive event or trend based at least in part on the measurement information.

According to certain example embodiments, the one or more processors 106 associated with the corrosivity sensing system 100 may be configured to access the memory 104, and may be further configured to execute the computer-executable instructions for monitoring corrosion or corrosive contaminants associated with the liquid fuel via the one or more sensors 122, 130. Example embodiments may utilize the prediction module 116 for predicting a cumulative level of corrosion in the or of the one or more components associated with a gas turbine 126 based at least in part on the monitoring, and outputting a signal associated with the monitoring. Example embodiments may also be configured for estimating a remaining lifetime associated with the one or more components.

Figure 2:
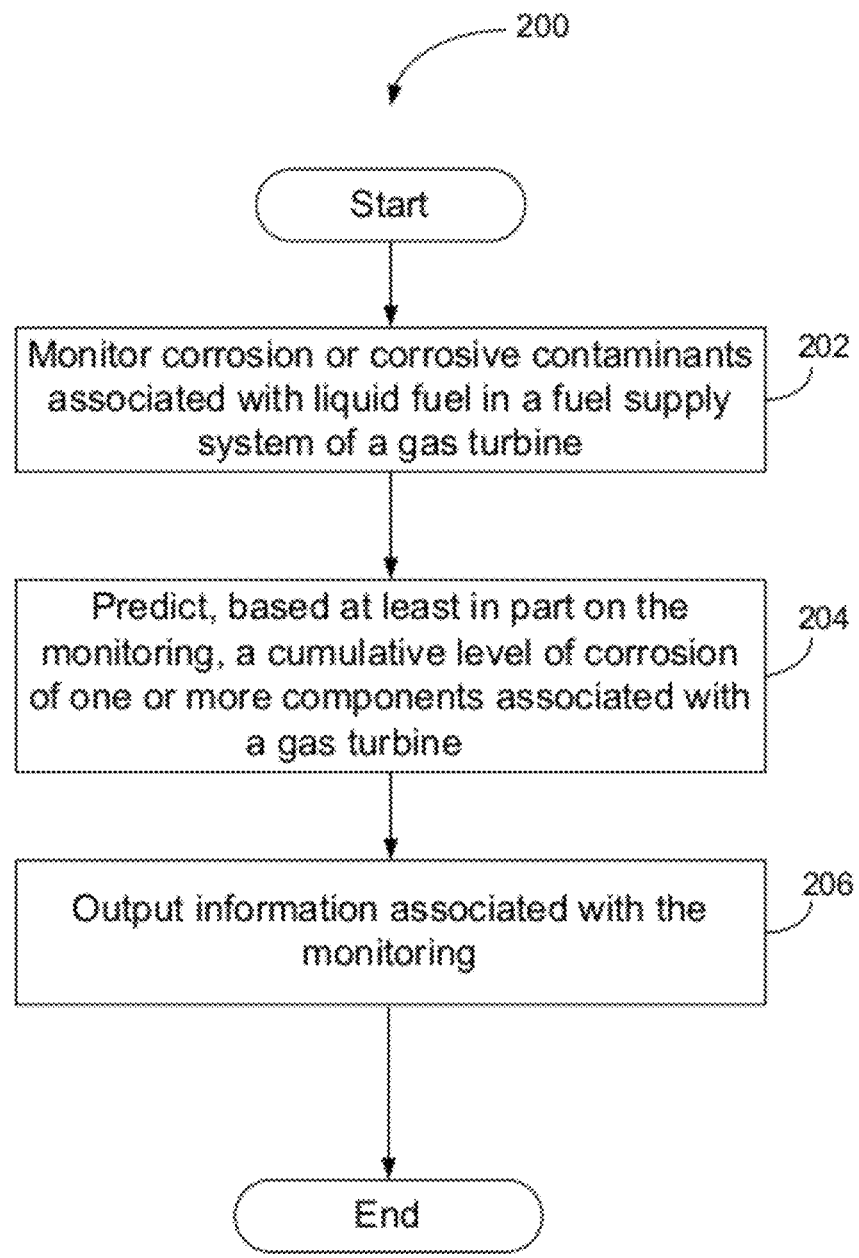
FIG. 2 is a flow diagram of an example method according to an example embodiment of the invention.

FIG. 2 is a flow diagram of an example method for monitoring and predicting corrosivity in liquid fuels according to an example embodiment of the invention. The method 200 starts in block 202 and includes monitoring corrosion or corrosive contaminants associated with liquid fuel in a fuel supply system of a gas turbine. In block 204 and according to an example embodiment, the method 200 includes predicting, based at least in part on the monitoring, a cumulative level of corrosion in the or of the one or more components associated with a gas turbine. In block 206 and according to an example embodiment, the method 200 includes outputting information associated with the monitoring. The method 200 ends after block 206.

Accordingly, example embodiments of the invention can provide the technical effects of creating certain systems, methods, and apparatus that monitor gas turbine fuel to provide corrosion information. Example embodiments of the invention can provide the further technical effects of predicting lifetimes of components associated with the gas turbine based on corrosion measurements. Certain example embodiments of the invention can provide the further technical effects of remediating or minimizing the damage done to gas turbine components by injecting one or more corrosion inhibitors into the fuel lines when corrosive contamination is detected. Example embodiments of the invention can provide the further technical effects of modifying maintenance schedules for the gas turbine components based on cumulative corrosion, predictions, and/or trends associated with the measurement of corrosion.

In example embodiments of the invention, the corrosive sensing system 100 may include any number of hardware and/or software applications that are executed to facilitate any of the operations. In example embodiments, one or more I/O interfaces may facilitate communication between the corrosive sensing system 100 and one or more input/output devices. For example, a universal serial bus port, a serial port, a disk drive, a CD-ROM drive, and/or one or more user interface devices, such as a display, keyboard, keypad, mouse, control panel, touch screen display, microphone, etc., may facilitate user interaction with the corrosive sensing system 100. The one or more I/O interfaces may be utilized to receive or collect data and/or user instructions from a wide variety of input devices. Received data may be processed by one or more computer processors as desired in various embodiments of the invention and/or stored in one or more memory devices.

One or more network interfaces may facilitate connection of the corrosive sensing system 100 inputs and outputs to one or more suitable networks and/or connections; for example, the connections that facilitate communication with any number of sensors associated with the system. The one or more network interfaces may further facilitate connection to one or more suitable networks; for example, a local area network, a wide area network, the Internet, a cellular network, a radio frequency network, a Bluetooth™ (owned by Telefonaktiebolaget LM Ericsson) enabled network, a Wi-Fi™ (owned by Wi-Fi Alliance) enabled network, a satellite-based network any wired network, any wireless network, etc., for communication with external devices and/or systems. As desired, embodiments of the invention may include the corrosive sensing system 100 with more or less of the components illustrated in FIG. 1.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

While the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method comprising:
    monitoring corrosion or corrosive contaminants associated with liquid fuel in a fuel supply system of a gas turbine using one or more sensors positioned in the fuel supply system;
    predicting, based at least in part on the monitoring, a cumulative level of corrosion of one or more hot gas path (HGP) components associated with the gas turbine; and
    outputting information associated with the monitoring.

2. The method of claim 1 wherein predicting the cumulative level of corrosion comprises estimating a remaining lifetime associated with the one or more HGP components.

3. The method of claim 1, further comprising performing preventive maintenance on the one or more HGP components associated with the gas turbine based at least in part on the monitoring.

4. The method of claim 1, further comprising injecting one or more corrosion inhibitors into the fuel supply system based at least in part on the monitoring.

5. The method of claim 1, wherein monitoring comprises conducting at least one of online, continuous, or in-situ measurements.

6. The method of claim 1, wherein monitoring comprises measuring corrosion or corrosive contaminants associated with the liquid fuel using one or more linear polarization resistance (LPR) sensors.

7. The method of claim 1, wherein monitoring comprises measuring corrosion or corrosive contaminants associated with liquid fuel using the one or more sensors, wherein the one or more sensors comprise at least one of linear polarization resistance (LPR) sensors, sacrificial electrodes, water sensors, density sensors, or viscosity sensors.

8. The method of claim 1, further comprising storing at least a portion of the information associated with the monitoring, and determining a corrosive event trend based at least in part on the stored information.

9. A system comprising:
    a gas turbine;
    at least one fuel supply line for delivering liquid fuel to the gas turbine, the at least one fuel supply line being in communication with one or more sensors;
    the one or more sensors positioned in the at least one fuel supply line;
    at least one memory for storing data and computer-executable instructions; and
    at least one processor configured to access the at least one memory and further configured to execute the computer-executable instructions for:
        monitoring, with the one or more sensors, corrosion or corrosive contaminants associated with the liquid fuel;
        predicting, based at least in part on the monitoring, a cumulative level of corrosion of one or more hot gas path (HGP) components associated with the gas turbine; and
        outputting a signal associated with the monitoring.

10. The system of claim 9, further comprising a fuel supply tank and one or more fuel supply sensors for monitoring corrosion or corrosive contaminants associated with the liquid fuel in the fuel supply tank, wherein the one or more fuel supply sensors comprise at least one of linear polarization resistance (LPR) sensors, sacrificial electrodes, water sensors, density sensors, or viscosity sensors.

11. The system of claim 9, wherein the at least one processor is further configured for estimating a remaining lifetime associated with the one or more HGP components.

12. The system of claim 9, further comprising a corrosion inhibition injector for injecting one or more corrosion inhibitors into the fuel supply system based at least in part on the monitoring.

13. The system of claim 9, wherein the at least one processor is further configured for modifying a maintenance schedule associated with the gas turbine based at least in part on the monitoring.

14. The system of claim 9, wherein the one or more sensors are configured for monitoring corrosion or corrosive contaminants associated with the liquid fuel by at least one of online, continuous, or in-situ measurements.

15. The system of claim 9, wherein the one or more sensors comprise at least one of linear polarization resistance (LPR) sensors, sacrificial electrodes, water sensors, density sensors, or viscosity sensors.

16. An apparatus comprising:
    at least one memory for storing data and computer-executable instructions; and
    at least one processor configured to access the at least one memory and further configured to execute the computer-executable instructions for:
        monitoring, with one or more sensors, corrosion or corrosive contaminants associated with liquid fuel in a fuel supply system of a gas turbine using one or more sensors positioned in the fuel supply system;
        predicting, based at least in part on the monitoring, a cumulative level of corrosion of one or more hot gas path (HGP) components associated with the gas turbine; and
        outputting information associated with the monitoring.

17. The apparatus of claim 16, wherein the at least one processor is further configured for estimating a remaining lifetime associated with the one or more HGP components.

18. The apparatus of claim 16, wherein the at least one processor is further configured for controlling a flow of corrosion inhibitor into the fuel supply system based at least in part on the monitoring.

19. The apparatus of claim 16, wherein the at least one processor is further configured for modifying a maintenance schedule associated with the gas turbine based at least in part on the monitoring.

20. The apparatus of claim 16, wherein the at least one processor is further configured for storing at least a portion of the information associated with the monitoring, and wherein the at least one processor is further configured for determining at least one corrosive event trend based at least in part on the stored information.

* * * * *